United States Patent [19]

Marlett et al.

[11] Patent Number: 4,730,070

[45] Date of Patent: Mar. 8, 1988

[54] STABILIZATION OF AMINE ALANES

[75] Inventors: Everett M. Marlett; Frederick W. Frey; Steven W. Johnston, all of Baton Rouge, La.; Herbert D. Kaesz, Los Angeles, Calif.

[73] Assignee: Ethyl Corporation, Richmond, Va.

[21] Appl. No.: 51,720

[22] Filed: May 20, 1987

[51] Int. Cl.$^4$ .............................................. C07F 5/06
[52] U.S. Cl. ................................................... 556/171
[58] Field of Search ........................................ 556/171

[56] References Cited

U.S. PATENT DOCUMENTS

| | | | |
|---|---|---|---|
| 2,680,059 | 6/1954 | Bragdon | 556/171 X |
| 3,159,626 | 12/1964 | Ashby | 260/242 |
| 3,541,125 | 11/1970 | Sims | 260/448 |
| 3,642,853 | 2/1972 | Murib et al. | 260/448 |
| 3,657,301 | 4/1972 | Motz et al. | 556/171 |
| 3,696,136 | 10/1972 | Nelson | 556/171 |
| 3,926,833 | 12/1975 | Hoffman et al. | 252/188 |
| 4,006,095 | 2/1977 | Hoffman et al. | 252/188 |
| 4,456,584 | 6/1984 | Gautreaux | 423/644 |
| 4,474,743 | 10/1984 | Marlett | 423/347 |
| 4,528,176 | 7/1985 | Nelson | 423/644 |

OTHER PUBLICATIONS

Ruff et al., J. Am. Chem. Soc. 82, 2141 (1960).
Ashby, Adv. Inorg. and Radiochem. 8, 283 (1966).

*Primary Examiner*—Paul F. Shaver
*Attorney, Agent, or Firm*—Donald L. Johnson; John F. Sieberth; Robert A. Linn

[57] ABSTRACT

Amine alane decomposition is catalyzed by titanium. This effect of titanium can be suppressed by treating it with a passivating agent such as air, nitrous oxide, carbon monoxide and alkyl nitrites. Such agents may be used (1) to treat titanium-containing $NaAlH_4$ preparations to be used in preparing amine alanes, or (2) to treat amine alanes containing titanium as an impurity, e.g. in finely divided form. Furthermore, the reaction of $NaAlH_4$, amine, and a halide substance to produce an amine alane can be conducted in the presence of a passivating agent.

11 Claims, No Drawings

STABILIZATION OF AMINE ALANES

FIELD OF THE INVENTION

This invention pertains to the stabilization of amine alanes, $AlH_3 \cdot NR_3$, wherein $NR_3$ is a tertiary amine.

It is known in the art that amine alanes can be produced by reacting $NaAlH_4$, a tertiary amine, and a haloaluminum reactant such as $AlCl_3$. It is also known that $NaAlH_4$ can be prepared from the elements using a titanium promoter. Moreover, it is known in the art that titanium present in the $NaAlH_4$ starting material makes the amine alane unstable. Stated another way, it is known in the art that titanium causes amine alanes to decompose, over time.

This invention comprises the discovery that the deleterious effect of titanium on amine alanes—which is taught in U.S. Pat. No. 4,474,743—is combated by such substances as oxygen, air, nitrogen oxides, carbon monoxide, and alkyl nitrites. These substances—referred to herein as passivating agents—retard the decomposition of amine alanes that is promoted or catalyzed by titanium, or a titanium-containing substance. Thus, the passivating agents of this invention conserve amine alanes by preventing or retarding decomposition caused by a titanium-induced process.

Accordingly, this invention can be considered as providing means which enhance the availability of amine alanes for any desired use; for example as starting materials for preparing silane. Moreover, this invention can be considered as providing means for treating titanium in order to passivate it.

This invention is particularly useful as a means to deactivate titanium in particulate form. Thus this invention can be used to passivate titanium in a fine state of subdivision.

Three important areas of application illustrate this invention. First, this invention can be used to treat an amine alane-containing mixture that also contains a titanium species. Second, this invention can be used to passivate titanium present in a $NaAlH_4$ preparation that is to be used for preparing an amine alane. Third, this invention can be used to passivate titanium when the amine alane is being produced. For example, as disclosed more fully below, an amine alane can be prepared from titanium-containing $NaAlH_4$, tertiary amine, and a halide reactant such as $NaAlCl_4$, $AlCl_3$, HCl or the like, after adding a passivating agent of this invention to the reaction zone.

PRIOR ART

Use of titanium and other promoters in the preparation of sodium aluminum tetrahydride has been described; see for example U.S. Pat. Nos. 4,456,584, and 4,528,176.

Preparation of amine alanes from metal hydrides such as $NaAlH_4$ and $NaH$ and the lithium analogs of these substances has also been described; see for example U.S. Pat. Nos. 4,006,905; 4,474,743 supra; Ruff et al, *J. Am. Chem. Soc.* 82, 2141 (1960); U.S. Pat. Nos. 2,680,509; 3,159,626; 3,541,125; 3,642,853; 3,926,833, and Ashby, *Adv. in Inorg. Chem. and Radiochem.* 8, 283, (1966).

U.S Pat. No. 4,474,743, loc. cit., relates to preparation of silane from amine alanes. As stated above, that patent also discloses that titanium has a deleterious effect on amine alane stability.

None of the above-cited art discloses that this deleterious effect can be reduced through use of the stabilizing, i.e. passivating, agents of this invention.

SUMMARY OF THE INVENTION

As stated above, the prior art teaches that titanium promotes preparation of $NaAlH_4$ from the elements. It also teaches that titanium utilized for this purpose can be added to the reaction zone alloyed with the aluminum reactant. When this expedient is employed, titanium from the alloy appears in finely divided form in the product mixture.

U.S. Pat. No. 4,474,743 teaches two methods to prevent the deleterious effect caused by this titanium: (1) remove the titanium from the $NaAlH_4$ by recrystallization of the metal hydride, or (2) filter the amine alane (made from the $NaAlH_4$) to remove by-product salts and other impurities. Both of these expedients yield good results and can be used if desired. This invention provides an alternative, chemical means to reduce or overcome the deleterious effect of titanium. Furthermore, the process of this invention can offer advantages over the methods of titanium removal taught by the above-cited U.S. Pat. No. 4,474,743.

For example, in industrial, large-scale operations, recrystallization of the sodium aluminum hydride can be prohibitively expensive. Furthermore, because of the small size of titanium particles in an $NaAlH_4$ preparation, it is difficult and/or expensive on an industrial scale to remove all of the titanium from an amine alane product. On storage, the amine alane can begin to decompose due to residual titanium present, and the resultant decomposition will reduce yields of product when the amine alane is employed as an intermediate. However, when this invention is used, for example by adding a gaseous passivating agent to a vessel containing amine alane with residual titanium, the decomposition is alleviated or retarded. Thus, the invention can be used by itself, or as a "back up" to removal of the deleterious titanium by filtration, and thereby alleviate or reduce problems caused by amine alane decomposition.

Summarizing the above, this invention comprises a chemical treatment for combating the deleterious effect that titanium and/or titanium-containing substance(s) has or have on amine alanes. In the process of this invention, a passivating substance is used to treat titanium, or titanium-containing substance, which can be present in a finely divided form. The titanium may be admixed with two types of complex hydrides: (i) sodium aluminum hydride, $NaAlH_4$, or (ii) an amine alane, $AlH_3 \cdot NR_3$ or mixtures of these substances. By the process of this invention, titanium—through some unknown mechanism or mechanisms—becomes passivated, i.e. made less reactive toward amine alanes. Thus, through use of this invention, the titanium-catalyzed decomposition of amine alanes is reduced, and the amine alane product can be converted into another valuable compound without an undesired reduction in yield caused by presence of titanium.

The mechanism or mechanisms by which the titanium is passivated is not clearly known. Moreover, it is not certain whether the cause of the decomposition is titanium or some titanium-containing compound, or mixture thereof. In this regard, titanium metal in the aluminum used for $NaAlH_4$ production becomes exposed to hydrogen during $NaAlH_4$ synthesis, and may react with the hydrogen to form a hydride of some sort. Also, titanium present when the $NaAlH_4$ is reacted to form an amine alane becomes exposed to amines as well as halogen-containing species such as $AlCl_3$, or HCl. Therefore, the titanium may react at least partially, with one or more of these materials, when exposed to the reaction environment. Consequently, it is conceivable that some material(s) formed from titanium during the course of the reaction(s) employed may initiate amine alane decomposition.

Therefore, although the invention is described herein as a means for combating a deleterious effect on amine alanes exacerbated by titanium, it is to be understood that this invention comprises a means for combating amine alane decomposition, whether it is caused by titanium metal, or by a titanium-containing substance, or by a mixture of the metal with one or more of such substances, or by a mixture of such substances. Moreover, it is also to be understood that this invention is not to be limited by any theory or theories concerning the mechanism(s) involved in passivation.

It has been discovered that the passivation provided by this invention can occur both before, during and after the amine alane is prepared. Furthermore, it is concluded from the small amount of passivating agent required, that the passivation provided by this process is probably a surface phenomenon, and that it is not necessary to react away all the titanium or titanium-containing species that catalyzes the decomposition of the amine alane. Stated another way, it is apparently unnecessary to transform the entire amount of titanium or titanium-containing substance into another substance; instead, it seems only necessary to passivate the surface of the deleterious catalyst(s).

Passivation according to preferred embodiments of this invention is readily carried out. Preferred passivators of this invention, such as air, oxygen, the nitrogen oxides, and carbon monoxide, are gases. These gases are readily added to the reaction zone using a stream of the selected material.

As stated above, the mechanism or mechanisms by which the deleterious catalyst is passivated by this invention are not clearly known. In light of work to date, there may be more than one mechanism involved. For example, the utility of air or oxygen suggests that some oxidative action takes place. On the other hand, utility of CO suggests that some complex with titanium is involved. The alkyl nitrites or nitrogen oxides could conceivably function by either an oxidative or a complexforming mechanism.

It is known that solutions of aluminum hydride undergo slow decomposition by autocatalysis upon storage. The autocatalytic species responsible for this behavior is believed to be by-product, particulate aluminum. Titanium, when present, can initiate the formation of aluminum by decomposition of amine alanes. Therefore, the passivating agents of this invention may play two roles. First, the passivating agents may deactivate the titanium species and thereby retard the formation of active, particulate aluminum. Second, they may deactivate the active aluminum, for example by reacting with it to form a more inert species such as aluminum oxide.

It is surprising that the process of the invention affords a beneficial result. As stated above, the process of this invention comprises addition of a passivating agent—all or most of which are reactive substances—to a system which is comprised of an $AlH_3$.amine complex or $NaAlH_4$. It is known that aluminum hydride species such as $NaAlH_4$ are highly reactive, confer Ashby, supra. Thus, a skilled practitioner could expect that the passivator would be scavenged by the aluminum hydride present, and would not be available for passivation of the titanium species.

The passivation afforded by this invention is especially beneficial when the mixture of titanium and amine alane is to be heated or maintained at a temperature above about 0°-20° C. The rate of amine alane decomposition is appreciable at mild temperatures, e.g. 40° C.

As taught in U.S. Pat. No. 4,474,743, supra, amine alanes are preferably made from crude $NaAlH_4$ if the product solution of $AlH_3.NR_3$ is filtered from by-product salts and other impurities. When this invention is used, no filtration is required. However, use of a combination of a filtration step and the passivation process of this invention gives enhanced protection against titanium-catalyzed decomposition of amine alanes. This enhanced protection can be greater than that achieved through either filtration or passivation used alone. Thus, the combination of filtration followed by treatment of the filtrate with a passivating agent comprises a highly preferred embodiment of this invention.

This invention is not limited to the passivation of titanium introduced into a reaction mixture as a promoter for $NaAlH_4$ preparation. Thus, the invention can be extended to the stabilization of amine alanes from titanium-induced decomposition, whatever the source of titanium. Furthermore, it is believed that this invention can be extended to passivation of other transition metal (and transition metal-containing) catalysts used in the formation of $NaAlH_4$. Such other catalysts are for example, vanadium, zirconium, or chromium, or compound(s) of these metals.

DESCRIPTION OF PREFERRED EMBODIMENTS

An embodiment of this invention comprises a process for reducing the rate of amine alane decomposition catalyzed by titanium, and/or a titanium-containing substance, said process comprising treating titanium that is in contact with an amine alane, with a passivating amount of a passivating agent selected from the class consisting of $O_2$, air, CO, nitrogen oxides, and alkyl nitrites.

Another embodiment of this invention comprises a process for reducing the rate of amine alane decomposition catalyzed by titanium, and/or a titanium containing substance, said process comprising treating a titanium-containing sodium aluminum tetrahydride with a passivating amount of $O_2$, air, CO, nitrogen oxides, or alkyl nitrites, and subsequently reacting the passivated $NaAlH_4$, thereby produced, to prepare an amine alane.

Thus, repeating what has been stated above, this invention comprises a method for stabilizing an amine alane before or after the amine alane has been produced. Furthermore, as pointed out above, this invention comprises the embodiment of preparing an amine alane and passivating the titanium present in the reaction zone by adding one or more passivating agents of this invention to the reaction zone containing the reactants. Thus, the passivation can begin before and/or extend after the amine alane synthesis is carried out.

In one aspect of this invention, the utility of the claimed process lies within the interrelationships arising from the following:

(1) Sodium aluminum tetrahydride is an economical starting material for the preparation of amine alanes.

(2) Sodium aluminum tetrahydride can be efficaciously produced by reacting the elements in the presence of a catalyst, and a titanium promoter.

(3) When the sodium aluminum tetrahydride — admixed with titanium or titanium containing substance(s) produced with the NaAlH$_4$ — is employed to produce an amine alane, the titanium or titanium-containing substance(s) also promote decomposition of the amine alane.

(4) This invention provides means for combating the decomposition.

Thus, this invention comprises an efficacious supplement to a process illustrated by the following reaction sequence:

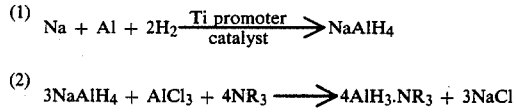

(2) $3NaAlH_4 + AlCl_3 + 4NR_3 \longrightarrow 4AlH_3 \cdot NR_3 + 3NaCl$

The process of equation (1) is efficaciously employed using somewhat elevated temperature and pressures. Hence, the process of equation (1) is usually conducted using a hydrogen pressure of at least 750 psi, and a reaction temperature of about 120° to about 160° C. Titanium is employed in a concentration of from about 300 to about 4000 (preferably 1000–2000) ppm, by weight, based on weight of aluminum. The amount of aluminum employed can be in stoichiometric excess.

The titanium used in equation (1) may be introduced into the reaction system as an alloy with the aluminum reactant. When NaAlH$_4$ produced by the process of equation (1) is used without removal of titanium admixed therewith in the process of equation (2), decomposition of the amine alane product can result. As indicated above, this invention comprises combating that decomposition by treating the reacting mixtures with one or more of the passivating agents of this invention either before, during or after the amine alane is produced.

With regard to equation (1), reference is made to U.S. Pat. Nos. 4,528,176 and 4,456,584, both of which relate to formation of NaAlH$_4$ using titanium as a promoter. The disclosure of those patents is incorporated by reference herein as if fully set forth.

Although preferred embodiments of this invention relate to NaAlH$_4$ produced by methods referred to above, it is to be understood that this invention is not dependent upon the method utilized to prepare the NaAlH$_4$. Naturally, this invention is primarily directed to passivation of titanium introduced into a reaction system through use of titanium promotion in NaAlH$_4$ synthesis. However, it is to be understood that this invention is directed to the prevention or reduction of the deleterious, titanium-induced effect on amine alanes without limitation based on how or why the titanium is contacted with the amine alane.

Much of the disclosure of this invention herein will relate to amine alanes produced from AlCl$_3$ and a tertiary amine. However, it is to be understood that the invention is not limited to amine alanes produced by this route. For example, the NaAlH$_4$ can be reacted with some species other than AlCl$_3$ such as HCl or NaAlCl$_4$, or the bromine or fluorine analogs of those substances. Moreover, this invention can be applied to amine alane preparation illustrated by Equation (d) in Column 2 of U.S. Pat. No. 4,474,743. As shown there (column 2, line 25) amine alanes can be made from a tertiary amine, and elemental aluminum and hydrogen.

Reaction of NaAlCl$_4$ with NaAlH$_4$ and a tertiary amine is the subject of application Ser. No. 782,972 filed Oct. 2, 1985, in the name of E. M. Marlett. Use of HCl as a reactant is the subject of another application for E. M. Marlett, Ser. No. 945,286, filed Dec. 22, 1986. This invention can also be extended to use with the method set forth in application Ser. No. 926,662 filed Nov. 4, 1986, in the name of E. M. Marlett & F. W. Frey. The disclosures in those documents are included by reference herein as if fully set forth.

As stated above, the process of this invention comprises treating (1) an amine alane, and/or (2) an amine alane precursor such as NaAlH$_4$, that is admixed with titanium. The process of this invention renders titanium less able to initiate amine alane decomposition. For purposes of this invention, the treatment of the titanium or titanium-containing substance(s) is termed "passivation", and the materials utilized for this purpose are called "passivating agents".

Various types of passivating agents are included within this invention. They include air, oxygen and oxides. Typically the oxides are oxides of a nonmetallic element such as carbon or nitrogen. The preferred oxides are simple, or binary compounds; i.e., they are solely composed of oxygen and the nonmetallic element. Such compounds are exemplified by carbon monoxide and:

| | |
|---|---|
| nitrous oxide | $N_2O$ |
| nitric oxide | $NO$ |
| nitrogen dioxide | $NO_2$ |
| dinitrogen tetroxide | $N_2O_4$ |

This invention also includes use of organic nitrites as passivating agents. These have the formula RONO wherein R designates an organic radical, e.g. alkyl. It is believed that the exact structure and size of the organic radical is not critical. Lower alkyl nitrites (RONO), wherein R is an alkyl group of one to ten carbon atoms are preferred. Preferred compounds of this type include methyl-, ethyl-, propyl-, n-butyl-, isoamyl-, n-hexyl-, n-octyl-, and n-decylnitrite.

The process of this invention comprises treatment of the titanium or titanium-containing species with enough passivating agent to achieve the desired effect. Based on the amount of titanium to be passivated one contacts the mixture to be treated with from about 0.1 to about 100 mole of passivating agent, preferably from 1 to about 25 mole, and more preferably from about 2 to about 10 mole, per each gram atom of titanium. Large excesses of passivating agent should be avoided since excess agent may react with NaAlH$_4$ or the amine alane.

A skilled practitioner can readily determine the desired amount of passivating agent required by use of routine experimentation. For example, one can determine a lower limit below which the desired effect is not achieved. Also, one can also determine an upper limit of the amount of passivating agent beyond which the passivating agent causes no more passivation or an unwanted deleterious effect.

The passivating agent can be contacted with the titanium to be passivated in any convenient manner. For example, when the passivating agent is a gas, it may be added as a gas stream to the zone that contains the titanium to be passivated. When added in this way, not all of the passivating agent contacts the titanium to be present. Therefore, one can use an excess of passivating agent to insure that passivation takes place. The passivating agents need not be added in pure form to the reaction zone. For example, one or more passivating agents can be mixed and added to the zone containing the titanium to be passivated. Also, the passivating agent can be admixed, i.e. diluted with an inert material such as nitrogen or a noble gas, e.g. helium, argon, neon and the like, and then admitted to the zone containing the titanium.

The process of this invention is preferably conducted under conditions which promote effective contact between the titanium material to be passivated and the passivating agent. For example, an inert liquid in which the titanium substance is suspended can be stirred, and a fine stream of gaseous passivating agent introduced into or over the reaction mass. Countercurrent contacting of the liquid/solid mixture with the gas stream can also be used.

The temperature at which the process of this invention is conducted is not critical. Generally speaking, it is preferred to use a convenient reaction temperature at which the desired passivation readily takes place. Furthermore, low temperatures that are difficult to obtain in an economical manner, or at which the passivation effect takes place at an undesirably slow rate, are undesired. Temperatures which are unnecessarily high, or at which some deleterious effect occurs are also undesirable. Generally speaking, the process of this invention can be conducted over a range of temperatures. A suitable temperature range is about $-5°$ to about $50°$ C. and a preferred range is about $10°$ to about $40°$ C. The temperature selected depends to some extent on the method of use of the invention. Thus one may treat $NaAlH_4$ at any temperature in which the $NaAlH_4$ is stable and not deleteriously affected by the passivating agent. If the invention is used while the amine alane is being prepared, one uses the reaction temperature at which the amine alane synthesis is carried out, e.g. $0°-40°$ C. If the invention is used to stabilize amine alane after it is made, the temperature used is the temperature to which the alane product is exposed. The process can be conducted at atmospheric, sub-atmospheric or super-atmospheric pressures. In general, atmospheric pressure is suitable when using reactants that are liquids at reaction temperatures. A preferred pressure range is 0.2 to 10 atmospheres, more preferably 1 to 2 atmospheres.

The reaction time is not a truly independent variable but is dependent at least to some extent on the other reaction conditions employed. Generally, the passivation is conducted using a contact time of from 1 minute to 24 hours, preferably from about 5 minutes to about 4 hours.

The following examples illustrate the process but do not limit it.

EXAMPLE A

A 100 mL, 3-neck, round bottom flask was equipped with a magnetic stirrer, dispensing funnel, and a thermometer, and cooled with an ice bath. The system was blanketed with nitrogen throughout the run. To the flask was added 5.35 g of one-day old $NaAlH_4$, prepared from aluminum powder containing 1900 ppm Ti and admixed therewith, and 12.0 g of toluene. To the funnel was added a mixture of 2.78 g of $AlCl_3$, 24.2 g of toluene, and 8.10 g of triethylamine.

The temperature of the vessel contents was 0° C. at the beginning of the reaction. There was an initial heat kick to 2.5° C. when the funnel contents were added to the flask. The temperature returned to 0.5° C. in about 7 minutes, and was maintained at that temperature throughout the addition period. The total time for addition of the funnel contents was about 30 minutes.

Following completion of addition, stirring was continued for about 120 minutes at 0° C. The ice bath was removed and stirring continued for another 90 minutes; during this period the temperature of the flask contents was 25°–28° C.

The flask contents were filtered at reduced pressure in a dry box. The filtrate weighed 44.78 g and was stored in a freezer over the weekend. Based on aluminum and active hydrogen analyses, the product yield was 98% and 88%, respectively (average 93%).

The process of this example demonstrates that a good yield of amine alane can be obtained from a $NaAlH_4$ starting material prepared by a process in which titanium was used as a promoter. It also demonstrates that it is not necessary to separate the solid titanium residue from the solid $NaAlH_4$ product in order to achieve a good yield of amine alane.

EXAMPLE B

The process of the above example was modified somewhat and three runs were conducted. In all three, a 25 mL reaction flask was used. It was equipped as described in the above example; except that an ice bath was not employed. In all three runs, the solution in the dispensing funnel was a mixture of 2.00 g of toluene, 0.23 g $AlCl_3$, and 0.67 g of triethylamine. In all three runs, the materials added to the reaction flask were 0.48 g of $NaAlH_4$ and 1.00 g of toluene. The $NaAlH_4$ was from the same preparation used in the above example, except in these runs the preparations were 4, 5, and 12 days old, respectively.

In these runs the reactions were conducted at 40° C. and the vessel contents maintained at that temperature.

To determine the percent decomposition of the $AlH_3 \cdot NEt_3$ product due to the presence of titanium, measurements were made of the hydrogen evolved from the reaction mass while the mass was maintained at 40° C. The results are reported in the following table. The times reported are the elapsed times measured from initiation of the addition of the funnel contents to the flask.

TABLE I

| | TITANIUM-INDUCED DECOMPOSITION OF $AlH_3 \cdot N(C_2H_5)_3$ | | | | |
|---|---|---|---|---|---|
| | PERCENT DECOMPOSITION | | | | |
| | 1 Hour | 2 Hours | 3 Hours | 4 Hours | 5 Hours |
| Run 1 | 3.3 | 9.8 | 14.4 | 17.8 | 20.7 |
| Run 2 | 2.0 | 7.1 | 10.5 | 13.1 | 14.9 |
| Run 3 | 5.7 | 9.8 | 13.1 | 15.4 | |

The results indicate that there is considerable decomposition of amine alane maintained at 40° C. in contact with titanium. Comparison with the previous example also indicates a lower temperature reaction will give a much better yield.

The stability using 12-day old $NaAlH_4$ is about the same as for 4- and 5-day old material. The results obtained for the four-hour period (18%, 13% and 15%) probably reflect the degree of variability between runs conducted at this small scale of operation.

Further studies indicated, that for $AlH_3.NEt_3$ in toluene solution in which the titanium was removed by filtration, the decomposition rate varied from 0.1% per day initially, to 2% per day after 12 days at 40° C. This is in contrast to the results in the table which indicate product from crude $NaAlH_4$ can undergo ~10% decomposition within two hours at 40° C.

Purified $NaAlH_4$ gives reaction mixtures which exhibit only 1% decomposition after 2 days, a rate reasonably close to that shown by filtered solutions of $AlH_3.NEt_3$. Crude $NaAlH_4$ made from aluminum containing relatively little Ti, also gives comparatively stable reaction mixtures.

The stability problem with $AlH_3.NEt_3$ is believed not only to be associated with the Ti present in the crude $NaAlH_4$, but possibly also to the strength of the amine alane complex. Tetramethylethylenediamine (TMEDA) is a stronger ligand than $Et_3N$, and should form a more stable adduct. The $AlH_3.TMEDA$ complex was prepared and, indeed, proved to be more stable than $AlH_3.NEt_3$ on storage at room temperature and at 40° C. However, addition of TMEDA to an $AlH_3.NEt_3$ reaction mixture did not improve its resistance to decomposition.

The utility of this invention can be put in an important context by the following. Early studies of the amine alane synthesis reaction revealed that when the $NaAlH_4$ feed was used asproduced, (a) the $AlH_3.NEt_3$ yield dropped to as low as 44%, (b) the reaction mixture proved to be very unstable to decomposition, and (c) filtered poorly. Two immediately suspect causes were residual active Ti and the hydrogenation catalyst, OMH-1 $NaAl(OCH_2CH_3)_2H_2$, the latter being normally absent in washed solvent-free sodium aluminum tetrahydride. However, a toluene wash to remove OMH-1 catalyst, with all solids retained, gave an even less stable reaction mixture; but the same treatment on a filter passing 40–60μ particulates did improve stability. In both cases, removal of solvent from the $NaAlH_4$ prior to reaction significantly improved resistance to decomposition. Yield of $AlH_3.NEt_3$ rose from 44% for the original $NaAlH_4$, to 86% for a preparation washed free of 40–60μ solids, and to 97% for the washed/dried product.

The volatiles that had been removed showed no unusual compounds upon analysis by gas chromatography/mass spectrometry, but they imparted instability to the stripped $NaAlH_4$ solids when reintroduced prior to reaction. This did not occur when the condensate was added to other samples of $NaAlH_4$. Similarly, addition of OMH-1 to previously isolated $NaAlH_4$ did not increase the decomposition rate for the $AlH_3.NEt_3$ reaction mixture.

Further work indicated that in filtered $NaAlH_4$ preparations, appreciable titanium was present in particle sizes less than about 60 microns. Hence, filtration removed material that was promoting decomposition but not all of it. Additional work suggested that the increase of stability found on removing volatiles in vacuo was the result of air accidentally introduced into the $NaAlH_4$ sample. This result was totally unexpected.

EXAMPLE 1

A 0.50 g sample of $NaAlH_4$ (prepared by using aluminum powder containing 1900 ppm Ti as a promoter) and 2.00 g of toluene were added to a 25 mL reaction flask fitted as above, and also with means for passing dry air over the contents of the flask. Air was passed over the neck of the flask for 19 hours while maintaining the mixture with stirring at ambient temperature.

A solution of 0.23 g $AlCl_3$, 1.50 g of toluene and 0.67 g of triethylamine was added to the flask at 40° C. This temperature was maintained while stirring. Gas evolution indicated the following percent decomposition:

| Time (hours) | % Decomposition |
| --- | --- |
| 1 | 0.04 |
| 2 | 0.07 |
| 3 | 0.14 |
| 4 | 0.25 |

The results indicate that the air treatment substantially lowered the amine alane decomposition rate, thereby demonstrating the passivating effect of air provided by this invention.

The passivation effect exemplified above is applicable when using a tertiary amine that forms an amine alane by complexing with aluminum hydride, $AlH_3$. For purposes of describing this invention, the amines that are employed are referred to herein as "complexing tertiary amines". Suitable complexing tertiary amines which may be utilized in the invention are liquids or low melting solids and include tertiary aryl, cycloalkyl, alkyl, alkenyl and aralkyl amines, including monoamines, diamines, triamines, etc. Typically, the amines of the present invention may be tetramethylethylenediamine, phenyldimethylamine, triethylenediamine, phenylmethylethylamine, tricyclohexylamine, or mixtures thereof, and other similar compounds. A more preferred class of amines for use in the invention are aliphatic tertiary amines, which include trialkylamine and trialkenylamine. Further, these amines may generally contain up to about 30 carbon atoms each, and preferably contain alkyl and alkenyl groups each having from 1 to about 10 carbon atoms. Thus, useful amines of this class are tri-n-butylamine; tri-sec-butylamine; dibutylpentylamine; n-butyl-n-octyl-sec-butylamine; tripentylamine; trihexylamine; trihexenylamine; trioctadecylamine; didecenylpentylamine; tridecenylamine; and the like, as well as mixtures thereof. A most preferred class of amines for use in the invention are those lower alkyl amines such as trimethylamine, N,N-dimethylethylamine, and particularly, triethylamine. By the term "lower" is meant that the alkyl groups each contain 6 carbon atoms or less. The above compounds may be readily prepared by procedures well known to those skilled in the art. Products of the present invention are these amines complexed with aluminum hydride.

Also usable complexing amines are the tertiary polyamines such as N,N,N',N'-tetramethylethylenediamine and 1,4-diazabicyclo[2.2.2]octane. Other tertiary mono- and polyamines are suitable, such as tri-n-propylamine, triisopropylamine, ethyldimethylamine, diethylmethylamine, tributylamine, dimethylpropylamine, N,N,N,',N'-tetramethyldiaminomethane, quinuclidine, methyl-1,4-diazabicyclo[2.2.2]octane, etc.

The passivating effect noted above is obtained when oxygen is used in place of air, and when from 0.1 to 100 mole of passivating agent is used per gram atom titanium, preferably 1–25 mole. Similarly, using CO, $N_2O$, NO, $NO_2$, $N_2O_4$, methylnitrite, or decylnitrite in a range discussed above, passivation of the titanium is also achieved.

EXAMPLE 2

(I) Baseline Run 1

Sodium aluminum tetrahydride, prepared by reacting Na, Al and $H_2$ at 2000 psig and employing 1900 ppm titanium (alloyed with the Al powder) as a promoter, was used in the process of this example. A sample of 20.0 g of dry $NaAlH_4$ solids, plus 187.6 g of $AlCl_3$ stock solution (prepared from 210 g $AlCl_3$, 670 g of $Et_3N$, and 1747 g of toluene) were reacted at ambient temperature in a 1L, creased, round bottom flask, while using a magnetic stirring bar to stir the mixture. Gas evolution was measured using a wet test meter.

(II) Baseline Run 2

The above procedure was repeated using 178.2 g of $AlCl_3$ stock solution, a 5% decrease in $AlCl_3$. Gas evolution was also measured using a wet test meter.

The total gas evolution, in liters, for both baseline runs are noted in the table below.

(III) Passivation with Carbon Monoxide

A reaction mixture having the same composition as Baseline Run 2 was used. Immediately after preparation of the reaction mixture, 50 mL of carbon monoxide (1 atm pressure) was added to the flask over about one minute. Thereafter, to measure amine alane decomposition, gas evolution was determined; as shown in the table below.

(IV) Passivation with Nitrous Oxide

Procedure (III) was followed employing instead of CO, 50 mL (1 atm pressure) of $N_2O$. As usual, gas evolution was used to detect amine alane decomposition; as shown in the following table:

TABLE II

Passivation of Titanium Measurement
For Two Hour Elapsed Time

| Run | Test | Total Gas Evolved (L.) |
| --- | --- | --- |
| (I) | Baseline | 2.97 |
| (II) | Baseline | 2.94 |
| (III) | CO | 0.12 |
| (IV) | $N_2O$ | 0.11 |

The passivating effect noted above can be achieved using 0.1 to 100 mole of CO, or other nitrogen oxide, air, oxygen, methylnitrite, or decylnitrite. The passivating effect can also be achieved when the passivating substances are used following the same procedure with amine alanes made from other complexing tertiary amines such as those mentioned above. The passivating effect can also be achieved when the $AlCl_3$ used in the example is substituted with $NaAlCl_4$, HCl or $SiCl_4$ as set forth in application Ser. Nos. 782,972, 945,286 and 926,662 supra.

EXAMPLE 3

To further demonstrate the effectiveness of a passivation agent of this invention, two samples of $AlH_3.NEt_3$ in toluene were used. One was made while using CO as a passivation agent, as in Example 2; the other was prepared without a passivation agent. Both reaction mixtures were filtered, but the filtrates were somewhat cloudy, showing that a minor amount of finely divided titanium was present in each sample. The sample of the non CO-treated material weighed 148.3 g, the sample of the CO-treated material weighed 171.6 g.

These samples were stored in round bottom flasks at 40° C. The flasks were connected to wet test meters to measure any gas evolved from the samples.

After about 5⅓ days, it was noted that some gas had been evolved from each flask—0.24 L from the CO treated material, and 0.84 L from the non-treated material.

Samples from each run (89.8 g of the CO-treated and 119.1 g of the non CO-treated amine alane preparations) were put in pressure bombs and pressured to 20 psig with CO. After venting the bombs to 1 atm pressure, they were replaced in the 40° C. bath.

After 25 days it was noted that 0.34 L of gas had evolved from the sample that had been made in the absence of CO, while none had evolved from the amine alane made in the presence of CO. Thus, treatment of the unstable triethylamine alane/toluene solutions with CO effectively stopped the autocatalytic decomposition of the alane complex even at 40° C. This shows that passivation with CO may be used on a triethylamine alane solution that has already been made and is decomposing, and thereby reduce or stop the decomposition, and preserve the complex. This passivation makes it unnecessary to refrigerate amine alane during storage.

In view of the detailed description of this invention given above, a skilled practitioner can devise modifications or variations of the invention. Such modifications and variations are considered equivalents of this invention, and to be within the scope and spirit of the appended claims.

We claim:

1. Process for reducing the rate of amine alane decomposition catalyzed by titanium, said process comprising treating titanium that is in contact with an amine alane with a passivating amount of a passivating agent selected from the class consisting of $O_2$, CO, nitrogen oxides, and alkyl nitrites.

2. Process for reducing the rate of amine alane decomposition catalyzed by titanium, said process comprising treating a titanium-containing sodium aluminum tetrahydride with a passivating amount of $O_2$, CO, a nitrogen oxide or alkyl nitrite, and subsequently reacting the passivated $NaAlH_4$ thereby produced to prepare an amine alane.

3. Process for reducing the rate of amine alane decomposition catalyzed by titanium, said process comprising treating a titanium-containing sodium aluminum tetrahydride with a passivating amount of air, and subsequently reacting the passivated $NaAlH_4$ thereby produced to prepare an amine alane.

4. Process of claim 1, wherein said titanium is within a reaction mixture in which the amine alane is produced by reacting titanium-containing $NaAlH_4$ with a tertiary amine and an aluminum halide reactant.

5. Process of claim 4 wherein said passivating agent is oxygen.

6. Process of claim 4 wherein said passivating agent is a nitrogen oxide.

7. A process of claim 6 wherein said oxide is $N_2O$.

8. A process of claim 4 wherein said passivating agent is CO.

9. Process for producing an amine alane product of enhanced stability, said process comprising reacting in the presence of titanium, sodium aluminum tetrahydride, an aluminum halide, and a complexing tertiary amine, while adding to the reaction zone a titanium-passivating amount of a passivating agent selected from $O_2$, air, CO, nitrogen oxides, and alkyl nitrites.

10. Process of claim 9 wherein said passivating agent is carbon monoxide.

11. Process of claim 9 wherein said passivating agent is nitrous oxide.

* * * * *